US010575777B2

(12) United States Patent
Ayers et al.

(10) Patent No.: US 10,575,777 B2
(45) Date of Patent: Mar. 3, 2020

(54) IN-EAR ELECTRICAL POTENTIAL SENSOR

(71) Applicant: BOSE CORPORATION, Framingham, MA (US)

(72) Inventors: Tegan M. Ayers, Waltham, MA (US); Lifun Lin, Lincoln, MA (US); Romain Kirszenblat, Allston, MA (US); Mikhail Ioffe, Newton, MA (US); Dale McElhone, Marlborough, MA (US); Christopher R. Paetsch, Cambridge, MA (US); Jack E. Read, Marlborough, MA (US); Andrew Farrell, Boston, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 15/680,695

(22) Filed: Aug. 18, 2017

(65) Prior Publication Data

US 2019/0053756 A1 Feb. 21, 2019

(51) Int. Cl.
*H04S 7/00* (2006.01)
*A61B 5/00* (2006.01)
(Continued)

(52) U.S. Cl.
CPC ........ *A61B 5/6803* (2013.01); *A61B 5/04001* (2013.01); *A61B 5/04004* (2013.01);
(Continued)

(58) Field of Classification Search
CPC ... A61B 5/6803; A61B 5/0478; A61B 5/0492; A61B 5/0496; A61B 5/4809; A61B 5/0488; A61B 5/1107; A61B 5/6817; A61B 5/163; A61B 5/4542; A61B 5/4812; A61B 5/4064; A61B 5/04012; A61B 5/0476; A61B 5/04001; A61B 5/1103; A61B 5/04004; A61B 5/6898; A61B 5/4836; A61B 5/486; H04R 1/1016; H04R 1/1041; H04R 2420/07; G06F 3/011; G06F 3/012;
(Continued)

(56) References Cited

U.S. PATENT DOCUMENTS

2011/0313310 A1 12/2011 Tomita et al.
2012/0002822 A1* 1/2012 Peissig .................... G06F 3/012
381/74
(Continued)

OTHER PUBLICATIONS

International Search Report and Written Opinion for International Application No. PCT/US2018/039492 dated Sep. 7, 2018, 13 pp.

*Primary Examiner* — Vivian C Chin
*Assistant Examiner* — Douglas J Suthers
(74) *Attorney, Agent, or Firm* — Patterson + Sheridan, LLP (57) ABSTRACT

Aspects of the present disclosure provide an audio product for obtaining biologically-relevant information associated with a user comprising. The audio product includes at least two electrodes, a processor, and an electroacoustic transducer coupled to the processor. The processor is configured to receive at least one signal affected by an action of the user obtained via the first electrode or the second electrode and take one or more actions based on the at least one signal. The at least one action may control another device, in an effort to provide hands-free control of the other device.

22 Claims, 8 Drawing Sheets

(51) Int. Cl.
   *A61B 5/0488* (2006.01)
   *A61B 5/11* (2006.01)
   *G06F 3/01* (2006.01)
   *A61B 5/16* (2006.01)
   *A61B 5/04* (2006.01)
   *A61B 5/0476* (2006.01)
   *A61B 5/0478* (2006.01)
   *A61B 5/0492* (2006.01)
   *A61B 5/0496* (2006.01)
   *H04R 1/10* (2006.01)

(52) U.S. Cl.
   CPC ........ *A61B 5/04012* (2013.01); *A61B 5/0476* (2013.01); *A61B 5/0478* (2013.01); *A61B 5/0488* (2013.01); *A61B 5/0492* (2013.01); *A61B 5/0496* (2013.01); *A61B 5/1103* (2013.01); *A61B 5/1107* (2013.01); *A61B 5/163* (2017.08); *A61B 5/4064* (2013.01); *A61B 5/4542* (2013.01); *A61B 5/486* (2013.01); *A61B 5/4809* (2013.01); *A61B 5/4812* (2013.01); *A61B 5/6817* (2013.01); *A61B 5/6898* (2013.01); *G06F 3/012* (2013.01); *G06F 3/013* (2013.01); *G06F 3/015* (2013.01); *G06F 3/017* (2013.01); *H04R 1/1016* (2013.01); *H04R 1/1041* (2013.01); *A61B 5/4836* (2013.01); *H04R 2420/07* (2013.01)

(58) Field of Classification Search
   CPC .......... G06F 3/013; G06F 3/014; G06F 3/015; G06F 3/016; G06F 3/017
   USPC .......................................................... 381/74
   See application file for complete search history.

(56) References Cited

U.S. PATENT DOCUMENTS

| | | |
|---|---|---|
| 2014/0148724 A1 | 5/2014 | Ungstrup et al. |
| 2014/0342338 A1 | 11/2014 | Imran et al. |
| 2015/0150498 A1 | 6/2015 | George et al. |
| 2015/0172832 A1* | 6/2015 | Sharpe .................. G06F 21/35 381/328 |
| 2017/0087364 A1* | 3/2017 | Cartledge .......... A61N 1/36014 |
| 2017/0180882 A1* | 6/2017 | Lunner .................. G06F 3/015 |

* cited by examiner

IN-EAR ELECTRICAL POTENTIAL SENSOR

BACKGROUND

Aspects of the present disclosure generally relate to wireless technology and using information collected via an audio product for hands-free control of another device, such as a wireless device.

Wearable devices are electronic devices that are configured to be worn on a user's body and perform various functions. According to an example, electrodes on a wearable device are used to measure electrophysiological signals. These electrophysiological signals can be used to identify patterns in, for example, a user's brain wave activity and identify abnormalities. The abnormalities may be used for diagnostic purposes, as they may be indicative of neurological disorders.

As the types of wearable technology increases and in-view of the projected advancements of wireless communications, including the Internet of Things, it may be beneficial to use collected electrical signals from a user of a wearable device for other purposes.

SUMMARY

Certain aspects provide an audio product for obtaining biologically-relevant information associated with a user. The audio product includes a first electrode placed on an ear tip of the audio product, a second electrode placed on the audio product, a processor coupled to the first and second electrodes, wherein the processor is configured to: receive at least one signal affected by an action of the user obtained via the first electrode or the second electrode, and take one or more actions based on the at least one signal, and an electroacoustic transducer coupled to the processor.

According to an aspect, the first electrode and the second electrode are placed on different earpieces of the audio product. According to an aspect, the first electrode and the second electrode are placed on a same earpiece.

According to an aspect, the ear tip comprises an umbrella shaped ear tip, configured to create a seal with an ear canal of the user.

According to an aspect, the at least one signal comprises at least one of: a change in electrical potential associated with the user or movement of the audio product. According to an aspect, the at least one signal comprises an electromyogram (EMG), electrooculogram (EOG), or electroencephalogram (EEG) associated with the user.

According to aspects, the processor is configured to infer a state of the user based on signals received via at least one of the first electrode or the second electrode. The one or more actions are taken based, at least in part, on the inferred state.

According to an aspect, inferring the state of the user includes detecting eye movement associated with the user from signals received via at least one of the first electrode or the second electrode and the one or more actions include controlling a wireless device based on the determined eye movement.

According to an aspect, the detected eye movement indicates one of sleep onset, non-rapid eye movement (NREM) sleep, or REM sleep associated with the user. The audio product controls another device based on the detected eye movement.

According to an aspect, the audio product wherein the processor is configured to associate an eye movement pattern of the user with a command for the wireless device, detect the eye movement pattern based on the signals, and wherein the wireless device is controlled based, at least in part, on the association.

According to an aspect, inferring the state of the user includes tracking the user's facial movements using signals received via at least one of the first electrode or the second electrode and the one or more actions comprise controlling a wireless device based on the user's facial movements.

According to an aspect, tracking the user's facial movements includes measuring jaw movements based on the signals. In response, to the measured jaw movements, the audio product determines the user is one of talking or chewing. The one or more actions include adjusting a volume of music played by the wireless device.

According to an aspect, the processor is configured to associate a facial movement pattern of the user with a command for the wireless device and detect the facial movement pattern based on the signals. The audio product is configured to control the wireless device based on the detected facial movement pattern.

According to an aspect, inferring the state of the user includes processing the received signals to determine the presence of alpha waves in the received signals and determining the user's eyes are closed in response to the determined presence of alpha waves. The one or more actions include a volume of music played by a wireless device or entering a low power mode at the wireless device.

Certain aspects provide a wearable audio product including an electroacoustic transducer for obtaining biologically-relevant information associated with a user. The wearable audio product includes a first electrode placed on an ear tip of the audio product, a second electrode placed on the audio product, and a processor coupled to the first and second electrodes, wherein the processor is configured to: receive signals affected by an action of the user obtained via the first electrode or the second electrode, identify a movement associated with the user based on the received signals; and control a wireless device based, at least in part, on the movement.

According to an aspect, the movement comprises a movement pattern. According to aspects, controlling the wireless device comprises one of adjusting a volume of an output of the wireless device or entering a low power state at the wireless device. According to an aspect, the signals affected by an action of the user include at least one of: electromyogram (EMG), electrooculogram (EOG), or electroencephalogram (EEG) associated with the user.

Certain aspects provide a wearable audio product including an electroacoustic transducer for obtaining biologically-relevant information associated with a user. The wearable audio product includes a first electrode placed on an ear tip of the audio product, a second electrode placed on the audio product, and a processor coupled to the first and second electrodes, wherein the processor is configured to: measure a change in electrical potential associated with the user and movement of the audio product based on signals obtained via the first electrode or the second electrode, identify a pattern of movements associated with the user based on the measured change and movement of the audio product, and control a wireless device based, at least in part, on the identified pattern.

According to an aspect, the pattern of movements is associated with one of eye movement, facial movement, or brain activity.

DETAILED DESCRIPTION

Aspects of the present disclosure relate to using an audio product, configured to collect biologically-relevant information associated with a user of the product, to control another device. As described herein, the audio product may receive at least one signal affected by an action of the user. In response to the signal, the earpiece may take one or more actions such as controlling another device. The other device may be any device configured to communicate with the audio product, including, for example, a smartphone, tablet computer, audio system, television, and so on.

The audio product described herein may be placed in a user's ear. Sources of electrical potentials at the ear canal include skeletal muscles (based, at least in part, on facial movements), ocular motion (based, at least in part, on eye movement), and brain activity. Recordings of these sources are electromyogram (EMG), electrooculogram (EOG) and electroencephalogram (EEG), respectively.

According to an example, the audio product receives at least one signal indicating a change in electrical potential associated with the user or at least one signal associated with movement of the earpiece itself. The at least one signal collected using the audio product may include an EMG, EOG, or EEG.

Any one or combination of the collected signals may be used to infer a state of the user or identify a pattern of behavior of the user. A state of a user is not absolute; accordingly, the collected information is used to determine, with an increased confidence level or an increased likelihood, a particular state of a user. Example states of a user include sleep onset, non-rapid eye movement (NREM) sleep, rapid eye movement (REM) sleep, or an emotional state. For example, smiling may signify an increased likelihood the user is happy or furrowed eyebrows may indicate an increased likelihood the user is frustrated.

The determined state of the user or an identified pattern of behavior is used to create a variety of user experiences. Stated otherwise, biopotential tracking via the audio product triggers actions to control another device, such as changing a type of music played, changing the volume of the music, skipping to a next song, triggering a low-power state at the other device, or triggering automatic speech recognition (ASR).

The audio product has at least two electrodes. As will be described in more detail herein, the electrodes may be placed on a same or different earpiece. One electrode may be used as a reference electrode while the other electrode may be used as a data-collecting electrode. The use of two electrodes allows the audio product to detect a change in biopotential associated with the user.

Figure 1:
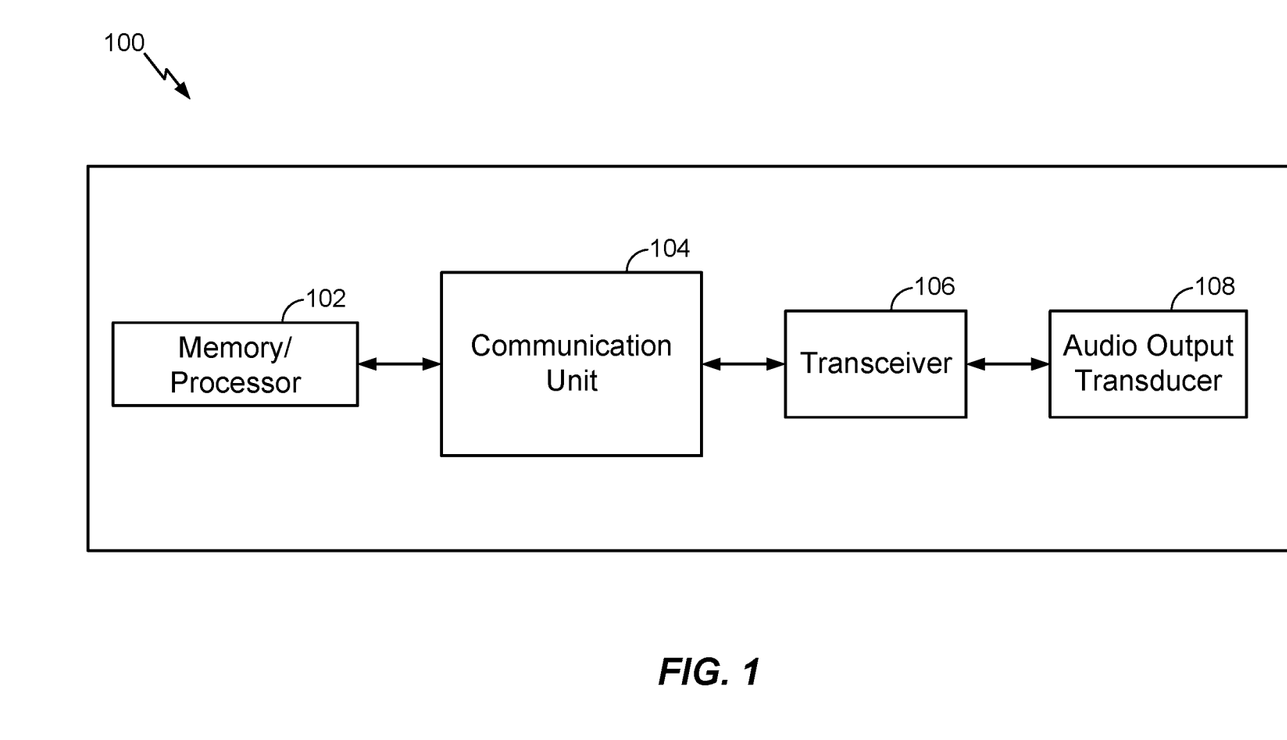
FIG. 1 is a block diagram of a wireless device.

FIG. 1 illustrates example components of an audio product 100, for example an earpiece. The audio product includes a memory and processor 102, communication unit 104, transceiver 106, and audio output transducer 108. The memory may include Read Only Memory (ROM), a Random Access Memory (RAM), and/or a flash ROM. The memory stores program code for controlling the memory and processor 102. The memory and processor 102 control the operations of the audio product 100. Any or all of the components in FIG. 1 may be combined into multi-function components.

The processor 102 controls the general operation of the audio product 100. For example, the processor 102 performs process and control for audio and/or data communication. In addition to the general operation, the processor 102 initiates processing signals received from electrodes of the audio product 100 to control the audio product 100 as described in more detail herein.

According to an example, the processor 102 includes a digital signal processor (DSP). Using a DSP, a variety of methods may be used to detect and differentiate between specific movements of the user. For example, algorithms may include matched and/or inverse filtering, correlation, or a classification algorithm using machine learning techniques (e.g., techniques such as neural networks, k-nearest neighbor algorithms, support vector machines, or regression-based classifiers). Algorithm decisions will depend on both the number and type of facial movements under detection, which signal features are used for classification, as well as the amount of data available for training. To handle person-to-person variation, according to aspects, the algorithm is adaptive, customizing itself to the specific user over time.

According to an example, pattern recognition algorithms are run locally in the audio product. Alternatively, pattern recognition algorithms are run on a device external to the audio product. The device external to the audio product is connected to the audio product through Bluetooth or another wireless communication protocol.

The communication unit 104 facilitates a wireless connection with one or more other devices. For example, the communication unit 104 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols.

The transceiver 106 transmits and receives information via one or more antennae to exchange information with one or more other wireless devices. According to aspects, the transceiver 106 includes one or more microphones. The transceiver 106 is not necessarily a distinct component. The transceiver 106 may be implemented entirely in software executed by the communication unit 104.

The audio output transducer 108 may be also known as a driver or speaker. In some examples, more than one output transducer is used. The transducer converts electrical signals into sound and converts sound into electrical signals.

Figure 2:
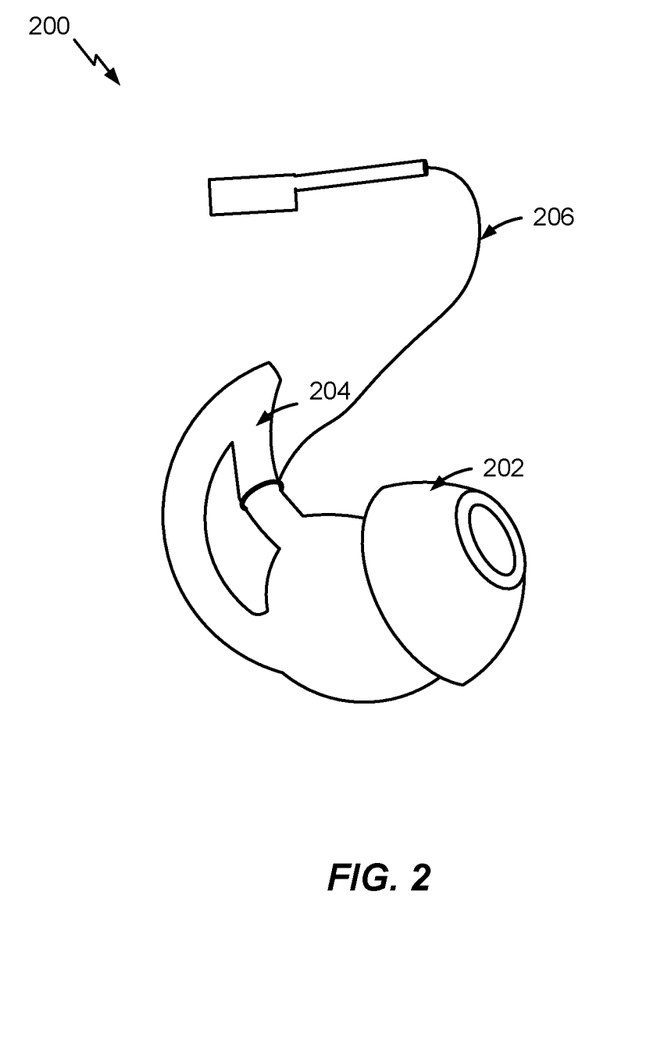
FIG. 2 illustrates an example earpiece having a flexible, umbrella-shaped ear tip.

FIG. 2 illustrates an example form factor of an audio product, such as the audio product illustrated in FIG. 1. As an example, the audio product comprises an earpiece 200. The earpiece 200 has a flexible, coated ear tip 202 and a tail portion 204, extending from the umbrella shaped tip. According to an example, the audio product may include two earpieces 200, one earpiece configured for each of the left and right ear of a user.

The ear tip provides enough surface area contact with the user's skin to collect a usable signal. The soft, flexible material of the tip helps the tip to conform to the ear geometry and increases the surface area having contact with a user's skin. Additionally, the flare of the umbrella shaped tip provides springiness so that some pressure is exerted by the tip on the skin to create a gentle seal with the user's ear canal. This pressure helps to lower the contact resistance between the coating of the ear tip and the ear tip itself. A flexible ear tip with the umbrella shape allows a mass-producible earpiece capable of conforming to the interior shape and form of a wide range of individual ear canals.

As illustrated in FIG. 2, the earpiece may optionally have a wire 206 running through the earpiece to convey one or more signals to external, electronic hardware. According to another example, the signals are wirelessly conveyed to external electronic hardware.

Figure 3:
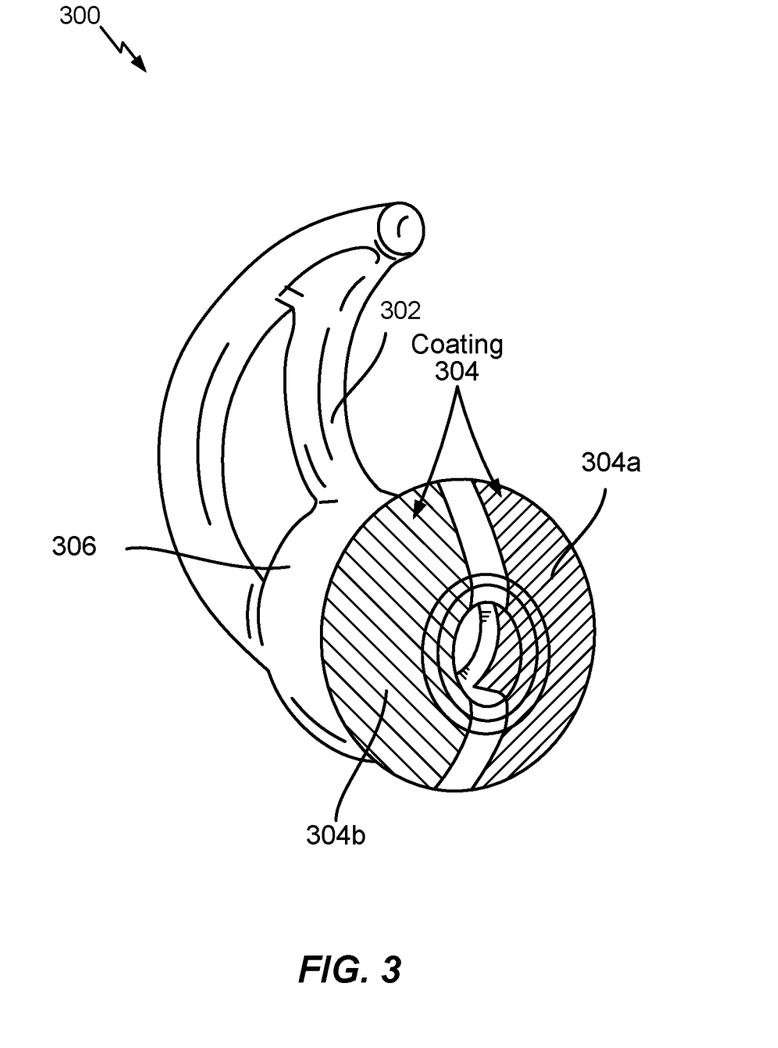
FIG. 3 illustrates an example earpiece.

FIG. 3 illustrates an example earpiece 300 including a coated, flexible, umbrella shaped ear tip and a tail portion. As illustrated in FIG. 3, the umbrella shaped ear tip is divided in two sections 304a and 304b. The tail is illustrated at 302. The housing 306 includes electronic hardware and a driver. According to one example, the housing is internal to the earpiece 300. For the earpiece to collect information associated with the user in an effort to control another device, the surface of the ear tip in contact with the skin of a user is conductive.

According to one example, the ear tip is coated with a conductive coating 304. The conductive coating can be continuous (which is not illustrated in FIG. 3) or may have more than one section. Each section 304a, 304b of the coating acts as a separate electrode used to collect information associated with a user. While two conductive coating sections are illustrated in FIG. 3, the earpiece 300 can have any integer number of conductive coatings. Having multiple electrodes is useful to compute EEG, EOG, or EMG as differences of potential. For example, one electrode may act as a reference electrode while the other electrode may act as a data-collecting electrode. Additionally, having several sections wherein each section acts as a separate electrode improves the signal to noise ratio by removing uncorrelated noise.

According to an aspect, the conductive coating functions as an electrode to collect information associated with the user. The coating material may be one of Ag, AgCl/Ag, conductive carbon, graphene, or other biocompatible conductive material. The ear tip coated with one of these conductive coatings may be used to collect information related to EEG, EOG, and EMG by contacting the skin of a user.

In one example, the umbrella shaped ear tip of the earpiece contacts an interior portion of an ear canal. According to another example, the entire earpiece, including the umbrella shaped ear tip and tail, are coated with a conductive coating. The conductive coating can be continuous or can have more than one section.

Figure 4:
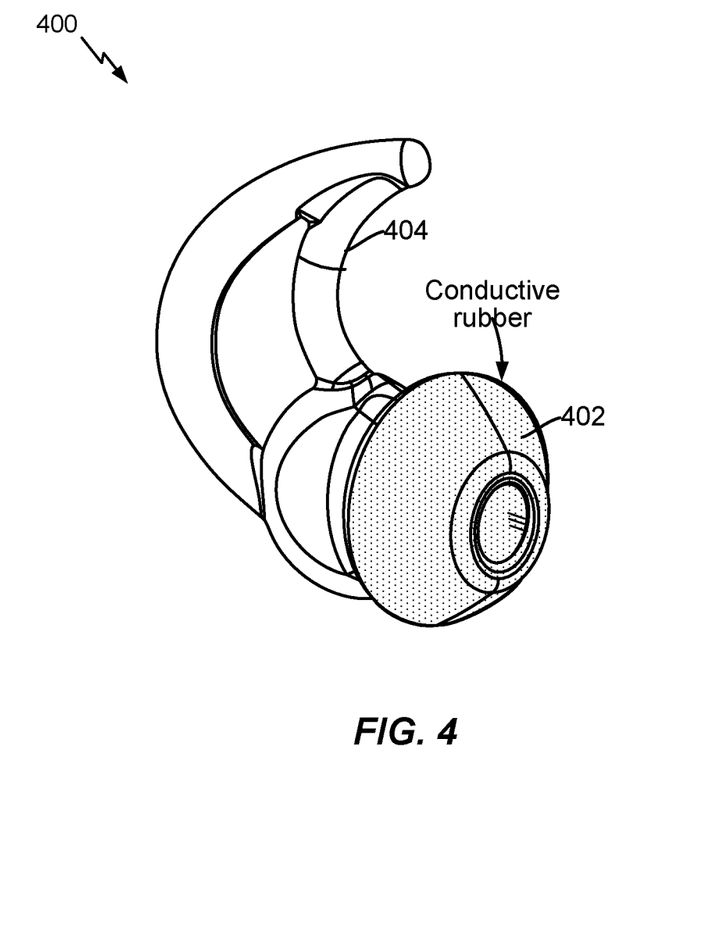
FIG. 4 illustrates an example earpiece.

FIG. 4 illustrates an example earpiece 400 having a flexible, umbrella shaped ear tip. In one example, the umbrella-shaped ear tip 402 is fabricated with conductive rubber and the tail 404 is fabricated with silicone. According to aspects, the conductive rubber used to fabricate the ear tip is made of a metal-filled substance such as silicone, polyurethane, or thermal plastic rubber. Using injection molding tools in the fabrication process of the ear tip, the conductive portions of the ear tip 402 can be electrically divided into several sections, wherein each section functions as an electrode. A conductive coating, as described with reference to FIG. 3, may be further added on top of the conductive rubber electrodes illustrated in FIG. 4.

According to another example, the entire earpiece 400 is fabricated with regular rubber and is entirely covered with a conductive rubber. According to aspects, the conductive rubber used to fabricate the earpiece is texturized before coating. Using injection molding tools in the fabrication process of the earpiece, the conductive portions of the earpiece can be electrically divided into several sections, wherein each section functions as an electrode.

As described above, the earpiece is made conductive by applying a coating (shown in FIG. 3) or by fabricating the earpiece or ear tip with a conductive material (shown in FIG. 4). According to aspects, other biosensors may be added to the earpiece. According to aspects, one or more optical sensors, microphones, or accelerometers are placed in the ear tip or in the housing internal to the earpiece.

Figure 5:
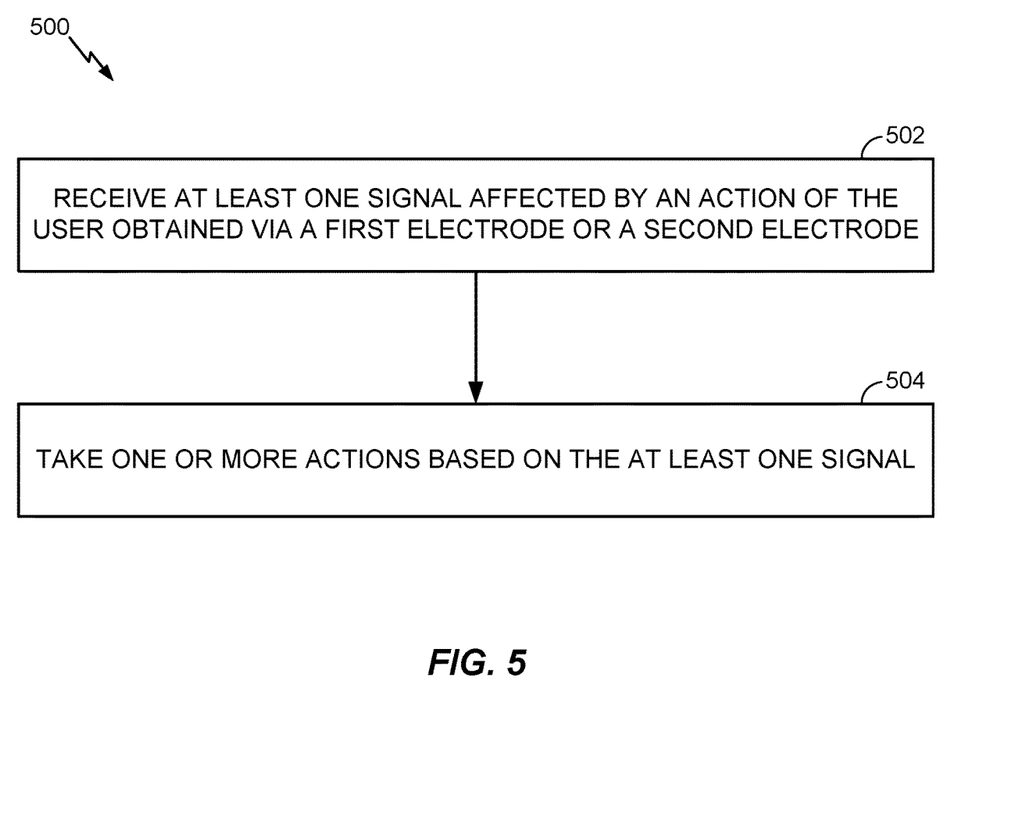
FIG. 5 illustrates example operations performed by an audio product.

FIG. 5 illustrates example operations 500 which may be performed by an audio product in accordance with aspects of the present disclosure. The audio product may include one or more components illustrated in FIG. 1. The audio product may include one or two earpieces. In one example, the first and second electrodes are located on a same earpiece. In another example, each earpiece has at least one electrode. One or both earpieces may include a flexible, umbrella shaped ear tip configured to create a seal with the user's ear canal.

At 502, the audio product receives at least one signal affected by an action of the user obtained via the first electrode or the second electrode. The first and second electrode may be located on the same earpiece of the audio product or on different earpieces of the audio product.

The at least one signal includes any combination of a change in electrical potential associated with the user or movement of the audio product itself. According to an example, the signal provides an indication of brain activity, muscle movement, and/or eye movement of a user. The signal may represent or be associated with an EMG, EEG, and/or EOG of the user.

According to aspects, the audio product may advantageously perform impedance tracking. Impedance tracking accounts for physical movement of the one or more electrodes. In this manner, the audio product detects one or a combination of movements of the one or more electrodes or a change in electrical potential associated with the user. As an example, if the user is chewing, the signals collected via the audio product may include both a change in electrical potential associated with jaw movement as well as movement of the audio product placed in the ear.

At 504, the audio product takes one or more actions based on the at least one signal. According to an example, the collected information is used to infer a state of the user. Based on the inferred state of the user, the audio product may intelligently and adaptively control another device.

The following examples of an audio product controlling another device are provided for illustrative purposes only. These non-limiting examples illustrate examples of how the audio product may control another device based on an inferred state of a user. The examples below describe example patterns the audio product may detect using collected signals. In response to a detected pattern, the audio product may perform a configured action to control the other device. The example patterns are provided as non-limiting examples. The audio product is configured to detect movement of the audio product and patterns associated with eye movement, facial movement, and brain activity.

Eye Movement

According to an example, the determined state of the user may be based on eye movement detected via at least one of the electrodes on the audio product. The detected eye movement may indicate an increased likelihood of sleep onset (characterized by slow, rolling eye movement), NREM sleep (characterized by little to no eye movement), or REM sleep (characterized with rapid eye movement) associated with the user. In response to the detected eye movement, the audio product may control another device. For example, the audio product may decrease the volume of an output of the other device or trigger the other device to enter a low power state in response to determining one or more of sleep onset, NREM sleep, or REM sleep.

According to another example, the audio product is configured to associate a pattern of behavior or movement of the user with a specific manner of controlling the other device. For example, the audio product may correlate a detected eye movement pattern with a command to change a song played on the other device. For illustrative purposes, the audio product may associate a detected "look left," "look center," and "look left" pattern with a command to decrease the volume of the audio product. Further, the audio product may associate a double "look left" with a command to change the song played by the other device. Upon detecting a configured pattern, the audio product may control the other device.

Figure 6:
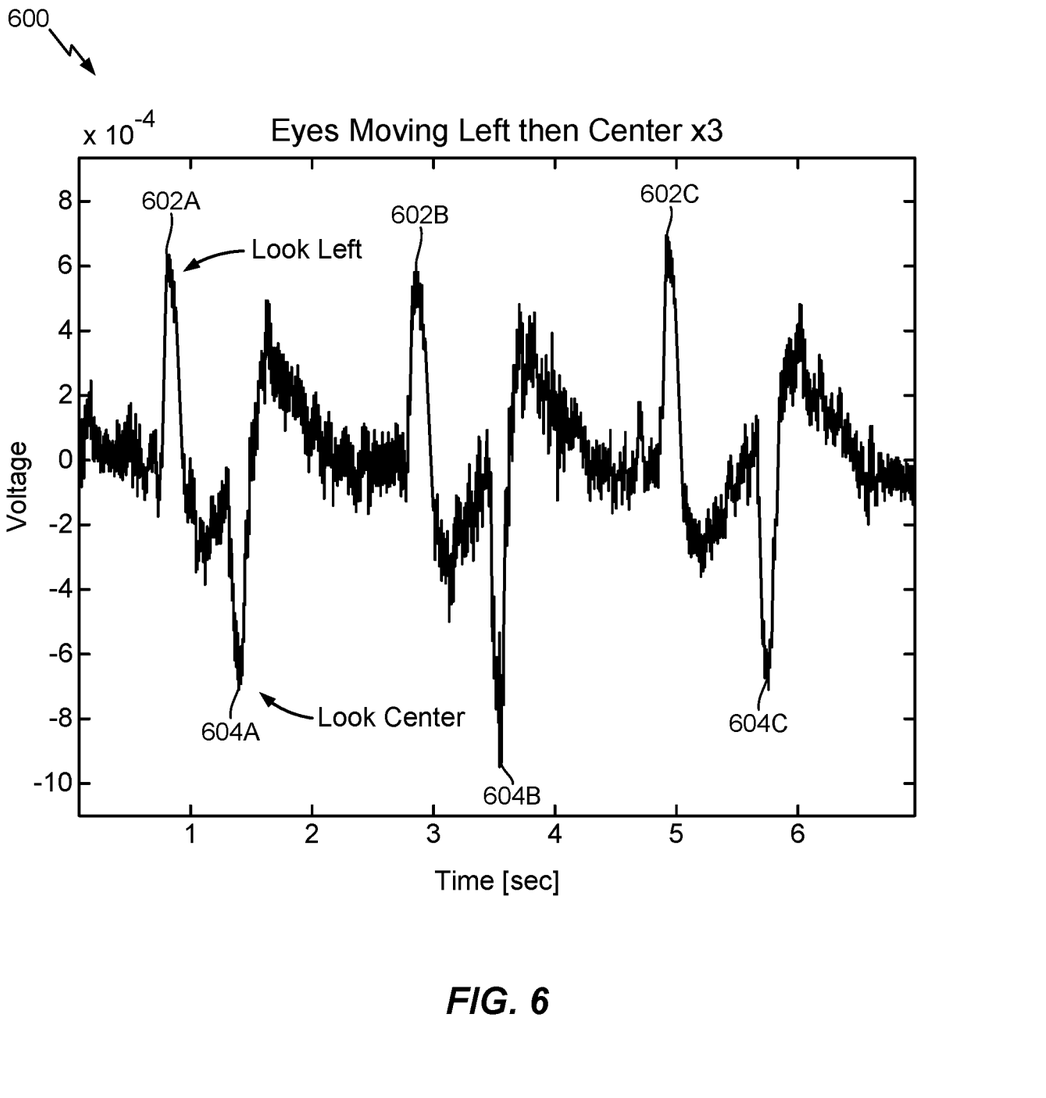
FIG. 6 illustrates an example plot of unfiltered EOG biosignals as measured from in-ear electrodes.

FIG. 6 illustrates an example plot 600 of unfiltered EOG signals collected using an audio product. The plot spikes to a high, positive voltage upon detection of a user looking left at 602A, 602B, and 602C. The plot dips to a negative voltage upon detection of a user returning their gaze back to center (for example, looking center) at 604A, 604B, and 604C. In one example, the audio product is configured to associate a pattern of eye movement from left to center three times to an action of triggering a low power mode at another device. Upon detection of a signal pattern similar to the plot illustrated in FIG. 6, the audio product takes action to trigger the low power mode at the other device.

Facial Movement

The audio product may infer a state of the user based on facial movements, which include, for example, smiling and jaw movements. The audio product may track a user's facial movements using signals received via at least one of the first electrode or the second electrode and control another device based on a detected movement. For example, the audio product may detect jaw movement. Jaw movements may indicate the user is one of talking, chewing, or grinding teeth during sleep. In response to detecting jaw movement, the audio product may adjust volume of music played by the wireless device. As an example, the audio product may decrease the volume of an output of the other device in response to determining that the user may be talking, chewing, or grinding teeth.

According to another example, the audio product is configured to associate a pattern of detected facial movement with a specific manner of controlling the other device. In response to detecting a configured pattern, the audio product may control the other device.

Figure 7:
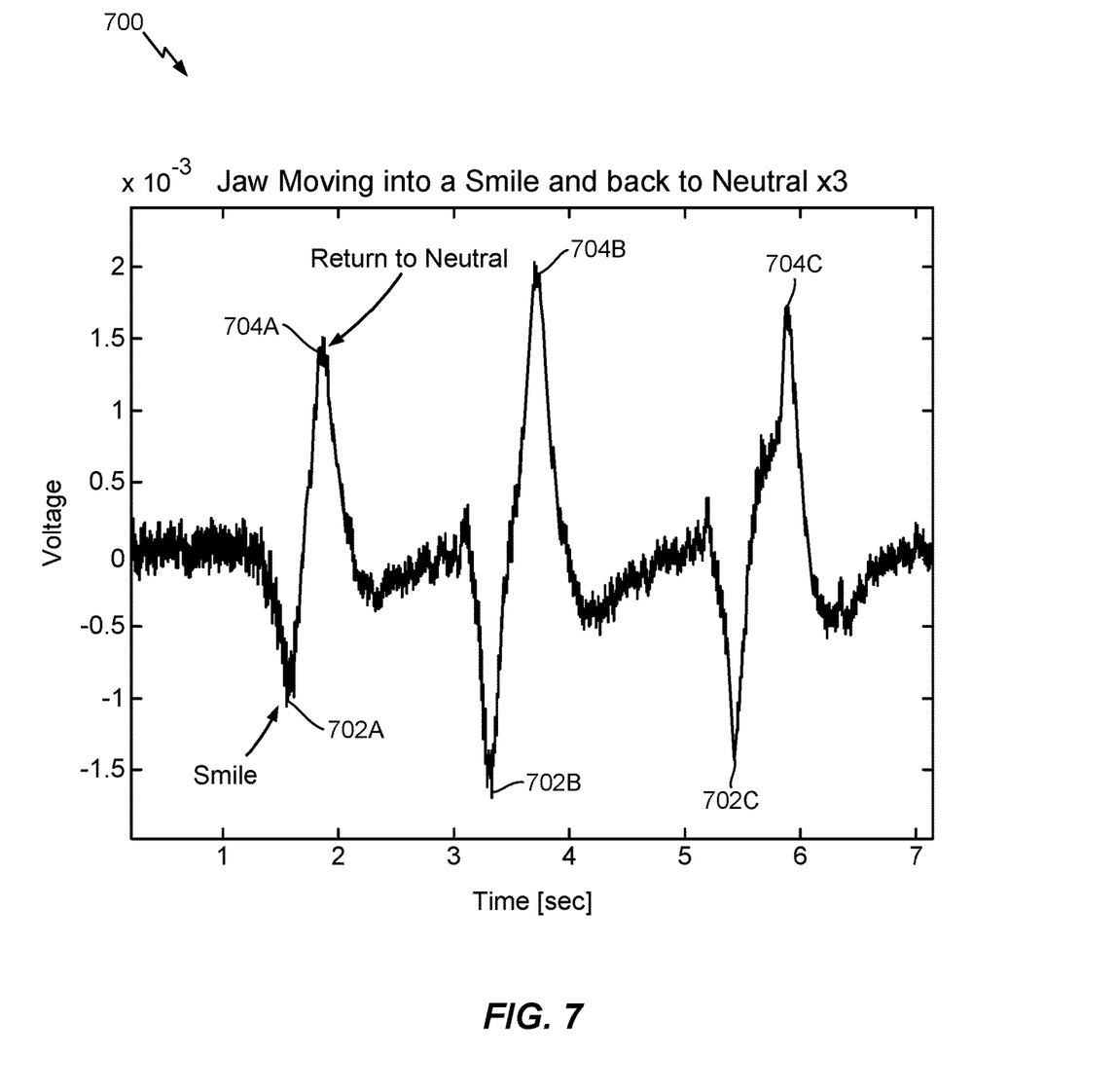
FIG. 7 illustrates an example plot of unfiltered EMG biosignals as measured from in-ear electrodes.

FIG. 7 illustrates an example plot 700 of unfiltered EMG signals collected using an audio product. The plot dips to a low voltage upon detection of a user smiling at 702A, 702B, and 702C. The plot spikes to a high voltage upon detection of a user returning to a neutral position at 704A, 704B, and 704C. In one example, the audio product is configured to associate a pattern of jaw movement from smiling to a neutral position three times to an action of decreasing the volume of an output of another device. Upon detection of a signal pattern similar to the plot illustrated in FIG. 7, the audio product takes action to trigger the change in volume.

Brain Activity

The audio product may infer a state of the user based on detected brain activity. Brain signals of interest may include alpha, theta, and delta waves. Alpha waves represent non-arousal. Theta waves typically have a greater amplitude and slower brainwave state as compared to alpha waves. Delta brainwaves are characterized by a greater amplitude and slower frequency as compared to theta waves. Alpha waves may indicate a user is relaxed. Theta waves may indicate the user is drowsy or idealizing. Delta waves may indicate a user is sleeping or dreaming.

Raw EEG signals collected from the ear are noisy. Alpha, theta, and delta waves are not easily visible without filtering. However, an accepted technique of determining if alpha waves (8-12 Hz) are present in a signal is to take the Fourier Transform of the collected biopotential when a user is resting.

Figure 8:
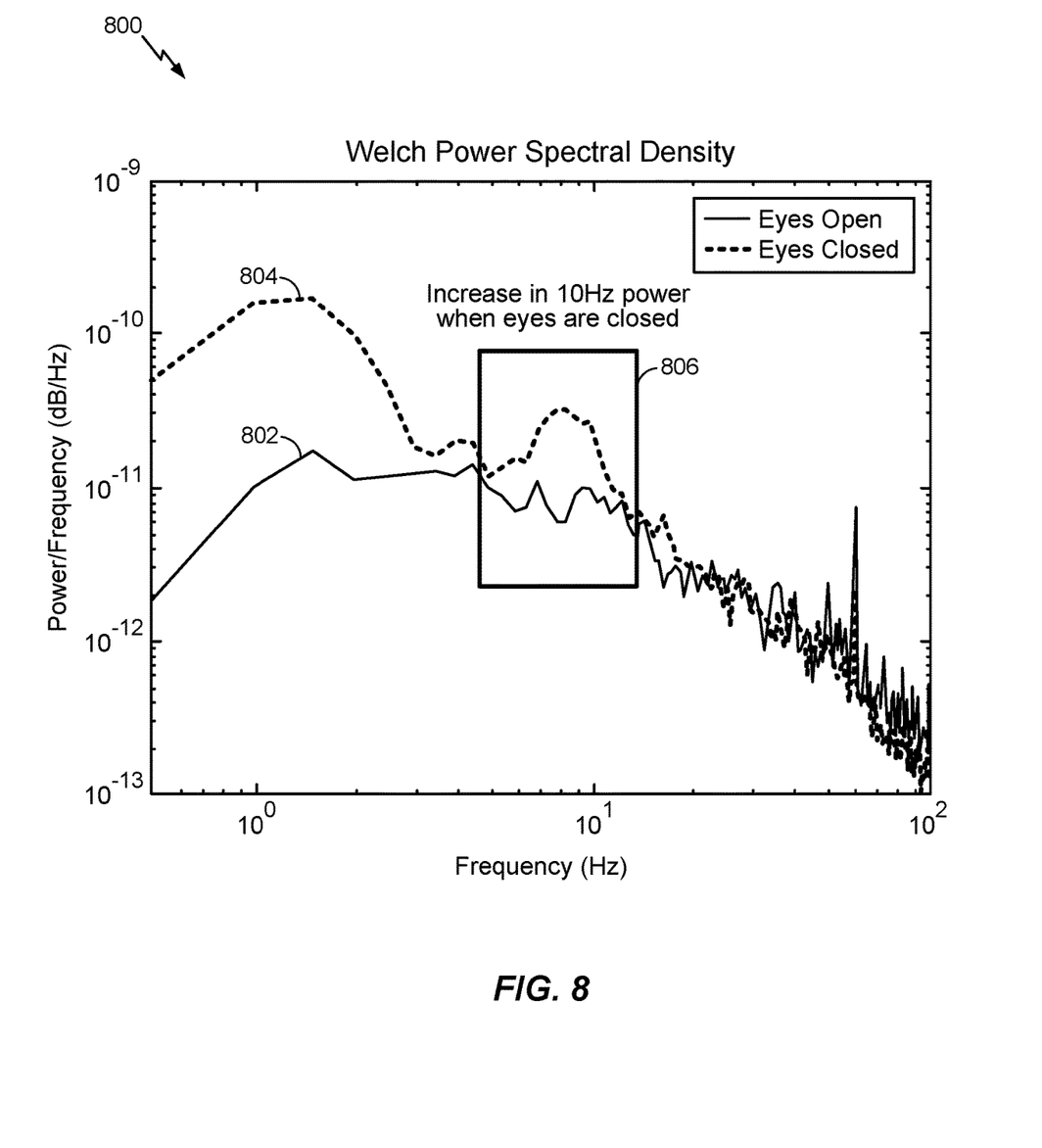
FIG. 8 illustrates an example plot of alpha brain activity when the user's eyes are closed.

FIG. 8 illustrates an example plot 800 of power versus frequency showing an increase in alpha brain activity (for example by 10 Hz) when the user's eyes are closed. 802 illustrates a plot of brain activity when the user's eyes are open. 804 illustrates a plot of brain activity when the user's eyes are closed. At 806, an increase 10 Hz power is shown when the user's eyes are closed as compared to when they are open. Detecting such an increase in power may indicate alpha brain waves, which may trigger the audio product to take one or more actions to control another wireless device.

Collecting brain activity from within the ear canal will help to enhance sleep stage predictions as each stage is characterized by a different brain wave pattern. For example, theta waves indicate N2 sleep and delta waves indicated N3 sleep. Upon detection of theta or delta waves, the audio product may take one or more actions to control another wireless device.

As described herein, an audio product may detect an action of a user. Based on the detected action, the audio product may take action to control another device. The other device may be a wireless device. In this manner, the audio product may create a variety of hands-free user experiences. Due to impedance tracking, the audio product may also account for movement of the audio product. Thus the signal or combination of signals obtained based on changes in electrical activity and/or movement of the electrode may be used to trigger control of another device.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. An audio product for obtaining biologically-relevant information associated with a user comprising:
   a first earpiece and a second earpiece;
   a first electrode placed on an ear tip of the first earpiece of the audio product;
   a second electrode placed on the audio product;
   a processor coupled to the first and second electrodes, wherein the processor is configured to:

receive at least one signal affected by an action of the user obtained via the first electrode or the second electrode, wherein the at least one signal indicates at least one of facial movements of the user or presence of alpha waves, infer a state of the user based on the at least one signal; and take one or more actions to wirelessly control a device external to the audio product based on the inferred state of the user, wherein taking the one or more actions comprises one of adjusting a volume of an output of the device external to the audio product or entering a low power state at the device external to the audio product; and an electroacoustic transducer coupled to the processor.

2. The audio product of claim 1, wherein the first electrode and the second electrode are placed on different earpieces of the audio product.

3. The audio product of claim 1, wherein the first electrode and the second electrode are placed on the first earpiece.

4. The audio product of claim 1, wherein the ear tip of the first earpiece comprises an umbrella shaped ear tip, configured to create a seal with an ear canal of the user.

5. The audio product of claim 1, wherein the at least one signal comprises at least one of: a change in electrical potential associated with the user or movement of the audio product.

6. The audio product of claim 1, wherein the at least one signal comprises an electromyogram (EMG), electrooculogram (EOG), or electroencephalogram (EEG) associated with the user.

7. The audio product of claim 1,
wherein the at least one processor is configured to infer the state of the user by detecting eye movement associated with the user from signals received via at least one of the first electrode or the second electrode, and
wherein the one or more actions comprise wirelessly controlling the device based on the detected eye movement.

8. The audio product of claim 7, wherein the detected eye movement indicates one of sleep onset, non-rapid eye movement (NREM) sleep, or REM sleep associated with the user.

9. The audio product of claim 7, wherein the processor is further configured to: associate an eye movement pattern of the user with a command for an external device;
detect the eye movement pattern based on the signals received via at least one of the first electrode or the second electrode; and
take one or more actions to wirelessly control the external device based, at least in part, on the association.

10. An audio product for obtaining biologically-relevant information associated with a user comprising:
a first electrode placed on an ear tip of the audio product;
a second electrode placed on the audio product;
a processor coupled to the first and second electrodes, wherein the processor is configured to:
receive at least one signal affected by an action of the user obtained via the first electrode or the second electrode;
infer a state of the user based on signals received via at least one of the first electrode or the second electrode, wherein inferring the state of the user comprises tracking facial movements of the user using signals received via at least one of the first electrode or the second electrode; and
take one or more actions to wirelessly control a device based on the at least one signal and the facial movements of the user; and
an electroacoustic transducer coupled to the processor.

11. The audio product of claim 10, wherein tracking the facial movements of the user comprises:
measuring jaw movements based on the signals; and
in response to the measured jaw movements, determining the user is one of talking or chewing,
wherein the one or more actions comprise adjusting a volume of music played by the device.

12. The audio product of claim 10, wherein the processor is configured to:
associate a facial movement pattern of the user with a command for the device; and
detect the facial movement pattern based on the signals, wherein controlling the device is based on the detected facial movement pattern.

13. The audio product of claim 10,
wherein inferring the state of the user comprises detecting eye movement associated with the user from signals received via at least one of the first electrode or the second electrode.

14. The audio product of claim 13, wherein the detected eye movement indicates one of sleep onset, non-rapid eye movement (NREM) sleep, or REM sleep associated with the user.

15. The audio product of claim 13, wherein the device comprises a device external to the audio product, and wherein the processor is further configured to: associate an eye movement pattern of the user with a command for the external device;
detect the eye movement pattern based on the signals received via at least one of the first electrode or the second electrode; and
take one or more actions to wirelessly control the external device based, at least in part, on the association.

16. An audio product for obtaining biologically-relevant information associated with a user comprising:
a first electrode placed on an ear tip of the audio product;
a second electrode placed on the audio product;
a processor coupled to the first and second electrodes, wherein the processor is configured to:
receive at least one signal affected by an action of the user obtained via the first electrode or the second electrode;
infer a state of the user based on signals received via at least one of the first electrode or the second electrode, wherein inferring the state of the user comprises processing the received signals to determine presence of alpha waves in the received signals, and determining eyes of the user are closed in response to the determined presence of alpha waves;
take one or more actions to wirelessly control a device based on the at least one signal, wherein the one or more actions comprises adjusting a volume of music played by the device or entering a low power mode at the device; and
an electroacoustic transducer coupled to the processor.

17. The audio product of claim 16, wherein the device comprises a device external the audio product.

18. A wearable audio product including an electroacoustic transducer for obtaining biologically-relevant information associated with a user comprising:
a first earpiece and a second earpiece;
a first electrode placed on an ear tip of the first earpiece of the audio product;

a second electrode placed on the audio product; and a processor coupled to the first and second electrodes, wherein the processor is configured to:

receive signals affected by an action of the user obtained via the first electrode or the second electrode, identify a movement associated with the user based on the received signals; and wirelessly control a device external to the audio product based, at least in part, on the movement, wherein controlling the device external to the audio product comprises adjusting a volume of an output of the device external to the audio product and entering a low power state at the device external to the audio product.

19. The wearable audio product of claim 18, wherein the movement comprises a movement pattern.

20. The wearable audio product of claim 18, wherein signals affected by an action of the user include at least one of: electromyogram (EMG), electrooculogram (EOG), or electroencephalogram (EEG) associated with the user.

21. A wearable audio product including an electroacoustic transducer for obtaining biologically-relevant information associated with a user comprising:

a first earpiece and a second earpiece;

a first electrode placed on an ear tip of the first earpiece of the audio product;

a second electrode placed on the audio product; and a processor coupled to the first and second electrodes, wherein the processor is configured to:

measure a change in electrical potential associated with the user and movement of the audio product based on signals obtained via the first electrode or the second electrode, identify a pattern of movements associated with the user based on the measured change and movement of the audio product; and wirelessly control a device external to the audio product based, at least in part, on the identified pattern, wherein controlling the device external to the audio product comprises adjusting a volume of an output of the device external to the audio product and entering a low power state at the device external to the audio product.

22. The wearable audio product of claim 21, wherein the pattern of movements is associated with one of eye movement, facial movement, or brain activity.

* * * * *